United States Patent
Iwasa et al.

(10) Patent No.: US 6,849,384 B2
(45) Date of Patent: Feb. 1, 2005

(54) PHOTOACID GENERATORS, PHOTORESIST COMPOSITIONS CONTAINING THE SAME AND PATTERING METHOD WITH THE USE OF THE COMPOSITIONS

(75) Inventors: Shigeyuki Iwasa, Tokyo (JP); Katsumi Maeda, Tokyo (JP); Kaichiro Nakano, Tokyo (JP); Etsuo Hasegawa, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 10/333,579

(22) PCT Filed: Jul. 23, 2001

(86) PCT No.: PCT/JP01/06325
§ 371 (c)(1),
(2), (4) Date: Jan. 24, 2003

(87) PCT Pub. No.: WO02/08833
PCT Pub. Date: Jan. 31, 2002

(65) Prior Publication Data
US 2003/0198889 A1 Oct. 23, 2003

(30) Foreign Application Priority Data
Jul. 25, 2000 (JP) ........................................ 2000-224661

(51) Int. Cl.$^7$ .......................... G03F 7/031; G03F 7/039; C07D 409/00; C07D 319/00; C07D 321/00

(52) U.S. Cl. .................... 430/281.1; 430/325; 430/326; 430/914; 430/921; 430/922; 549/9; 549/10; 549/13; 549/14; 549/80; 568/38; 568/58; 568/59

(58) Field of Search .............................. 430/281.1, 325, 430/326, 914, 921, 922; 549/9, 10, 13, 14, 80; 568/38, 58, 59

(56) References Cited

U.S. PATENT DOCUMENTS 3,426,046 A * 2/1969 Hatch ........................... 568/38
6,602,647 B2 * 8/2003 Iwasa et al. ................. 430/922

FOREIGN PATENT DOCUMENTS

| JP | 02-027660 | 1/1990 |
| JP | 07-028237 | 1/1995 |
| JP | 07-092675 | 4/1995 |
| JP | 08-259626 | 10/1996 |
| JP | 10-073919 | 3/1998 |
| JP | 11-133607 | 5/1999 |

(List continued on next page.)

OTHER PUBLICATIONS

Takechi, et al., "Alicyclic Polymer for ArF and KrF Excimer Resist Based on Chemical Amplification", Journal of Photopolymer Science and Technology, vol. 5, No. 3, 1992, pp. 439–446.

(List continued on next page.)

*Primary Examiner*—Richard L. Schilling
(74) *Attorney, Agent, or Firm*—McGinn & Gibb, PLLC

(57) ABSTRACT

Photoacid generators comprising sulfonium salt compounds represented by the following general formula (2) wherein $R^1$ and $R^2$ represent each an alkyl group optionally having oxo, or $R^1$ and $R^2$ may be cyclized together to form an alkylene group optionally having oxo; $R^3$, $R^4$ and $R^5$ represent each hydrogen or a linear, branched, monocyclic, polycyclic or crosslinked cyclic alkyl group; and $Y^-$ represents a counter ion.

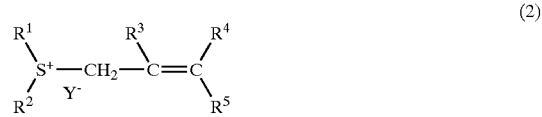

(2)

19 Claims, 1 Drawing Sheet

FOREIGN PATENT DOCUMENTS

| | | |
|---|---|---|
| JP | 2000-026446 | 1/2000 |
| JP | 2000-063433 | 2/2000 |
| JP | 2000-122296 | 4/2000 |
| WO | WO 00/11041 | 3/2000 |

OTHER PUBLICATIONS

R.D. Allen, et al., "Resolution and Etch Resistance of a Family of 193 nm Positive Resists", Journal of Photopolymer Science and Technology, vol. 8, No. 4, 1995, pp. 623–636.

R.D. Allen, et al., "Progress in 193 nm Positive Resists", Journal of Photopolymer Science and Technology, vol. 9, No. 3, 1996, pp. 465–474.

Crivello, et al., "A New Preparation of Triaryisulfonium and Selenonium Salts Via the Copper (II)–Catalyzed Arylation of Sulfides and Selenides with Diaryliodonium Salts", Journal of the Organic Chemistry, vol. 43, No. 15, 1978, pp. 3055–3058.

J.V. Crivello, et al., "New Photoinitiators for Cationic Polymerization", Journal of the Polymer Science, Symposium No. 26, 1976, pp. 383–395.

Noziaki, et al., "New Protective Groups in Alicyclic Methacrylate Polymers for 193–nm Resists", Journal of Photopolymer Science and Technology, vol. 10, No. 4, 1997, pp. 545–550.

Yamachika, et al., "Improvement of Post–Exposure Delay Stability in Alicyclic ArF Excimer Photoresists", Journal of Photopolymer Science and Technology, vol. 12, No. 4, 1999, pp. 553–560.

T. Naitoh, "The 8th Research Group on Polymers for Microelectronics and Photonics", Proceddings, 1999, pp. 16–18.

Nakano, et al., "Transparent Photoacid Generator (ALS) for ArF Excimer Laser Lithography and Chemically Ampligied Resist", Proceeding of SPIE, vol. 2195, 1994, pp. 194–204.

Nakano, et al., "Positive Chemically Amplified Resist for ArF Excimer Laser Lithography Composed of a Novel Transparent Photoacid Generator and an Alicyclic Terpolymer", Proceedings of SPIE, vol. 2438, 1995, pp. 433–444.

Houlihan, et al., "A Commercially Viable 193 nm Single Layer Resist Platform", Journal of Photopolymer Science and Technology, vol. 10, No. 3, 1997, pp. 511–520.

Iwasa, et al., "Chemically Amplified Negative Resists Based on Alicyclic Acrylate Polymers for 193–nm Lithography", Journal of Photopolymer Science and Technology, vol. 12, No. 3, 1999, pp. 487–492.

* cited by examiner

US 6,849,384 B2

PHOTOACID GENERATORS, PHOTORESIST COMPOSITIONS CONTAINING THE SAME AND PATTERNING METHOD WITH THE USE OF THE COMPOSITIONS

TECHNICAL FIELD

The present invention relates to a photoacid generator, a photoresist composition containing the same and a patterning method using the composition. More particularly, it relates to a photoacid generator suitable for photolithography using a far UV ray, typically represented by an ArF excimer laser, as a ray of light for exposing, a photoresist composition containing the photoacid generator, and a patterning method using the composition.

BACKGROUND ART

In manufacture of semiconductor devices such as typical LSIs (Large Scale Integrated circuits), photolithography technology is necessarily used to pattern insulating films such as silicon oxide and silicon nitride films formed on a semiconductor substrate into desired shapes. It is also used to pattern conductive films such as aluminum alloy and copper alloy films and a work itself including the semiconductor substrate.

In the photolithography, a UV-sensitive photoresist is applied on the work to form a photoresist film, to which a UV ray is radiated (which is exposed to a UV ray) through a mask pattern to turn a UV-radiated region into a soluble one (positive type) or an insoluble one (negative type). The photoresist film is then subjected to a developing process to partially remove the soluble one with a solvent for forming a resist pattern. Then, using the resist pattern as a mask, the work is selectively etched for patterning.

As an LSI is required to have a higher degree of functionality and performance, it is carried out to achieve a higher concentration and integration. Therefore, a need for photolithography technology to form fine circuit patterns becomes stricter. As a means for fine patterning, it is known to shorten a wavelength of a lithographic source for generating an exposing ray of light. For example, in mass production of a DRAM (Dynamic Random Access Memory) of 256 M bits through 1 G bits (its process size ranging from 0.25 $\mu$m to 0.15 $\mu$m), a far UV ray consisting of a KrF excimer laser ray of shorter wavelength (wavelength: 248 nm) is used instead of a UV ray consisting of an i-ray of the conventional type (wavelength: 365 nm).

In manufacture of a DRAM with an integration density of 4 G bits or greater (its process size being equal to 0.15 $\mu$m or less) that requires a fine pattern technology, a light source is required to radiate a far UV ray with a much shorter wavelength. In such a case, it is considered effective to use an ArF excimer laser ray (wavelength: 193 nm) and an $F_2$ excimer laser ray (wavelength: 157 nm) in photolithography.

In particular, the photolithography using an ArF excimer laser ray (ArF excimer laser lithography) is an effective candidate for the next-generation fine patterning technology following to the KrF excimer laser lithography and is now increasingly studied. For example, Takechi et al., Journal of Photopolymer Science and Technology, vol. 5, No. 3, pp. 439–446 (1992); R. D. Allen et al, Journal of Photopolymer Science and Technology, vol. 8, No. 4, pp. 623–636 (1995) and vol. 9, No. 3, pp. 465–474 (1996).

In addition to a high resolution corresponding to the micro-patterned process size, a high sensitivity is required for the resists for lithography using the above-mentioned ArF and $F_2$ excimer lasers, due to background situations such as a gas for use as a raw material in the laser oscillation having a short lifetime, an expensive lens being necessary, and the lens being able to be damaged easily by the laser. High sensitive photoresists suitable for such needs include a well-known chemically amplified resist that utilizes a photoacid generator as a photosensitive agent. The chemically amplified resist has a characteristic that allows the photoacid generator contained therein to generate a protonic acid due to light radiation. The protonic acid causes an acid catalytic reaction with a base resin and so forth in the resist by heating treatment after exposure. As a result, an extremely high sensitivity is achieved compared to that of a conventional resist that has a photoreaction efficiency rate (a reaction number per photon) less than 1.

As a typically known example of the chemically amplified resist, JP 2-27660A publication discloses a resist consisting of a combination of triphenylsulfonium hexafluoroarsenate and poly(p-tert-butoxycarbonyloxy-α-methylstyrene). Most of currently developed resists are of the chemically amplified type and thus development of high sensitive materials corresponding to shortened wavelengths of exposing sources is essentially required.

The above-mentioned chemically amplified resists used are classified into the positive and negative types. Among those, the chemically amplified resists of the positive type comprise at least three components: (1) a photoacid generator; (2) a base resin containing a group decomposable with acids; and (3) a solvent. On the other hand, the chemically amplified resists of the negative type are classified into two: one that essentially requires a crosslinking agent; and the other that requires no crosslinking agent. The former comprises at least four components: (1) a photoacid generator; (2) a base resin capable of reacting with a crosslinking agent; (3) a crosslinking agent; and (4) a solvent. The latter comprises at least three components: (1) a photoacid generator; (2) a base resin containing a crosslinking group; and (3) a solvent.

Examples of the photoacid generator that serves an important role in such chemically amplified resists include triphenylsulfonium salt derivatives as described in Journal of the Organic Chemistry, vol.43 (No. 15), pp. 3055–3058 (1978); alkylsulfonuim salt derivatives such as cyclohexylmethyl(2-oxocyclohexyl)sulfonium trifluoromethanesulfonate as disclosed in JP 7-28237A publication; and diphenyliodonium salt derivatives and succinimide derivatives as described in Journal of the Polymer Science, vol. 56, pp. 383–395 (1976).

Particularly, in the ArF excimer laser lithography, the most widely used photoacid generators at present are sulfonium salt compounds. Among those, triphenylsulfonium salt derivatives are most widely used currently. For example, see Nozaki et al., Journal of Photopolymer Science and Technology, vol.10 (No.4), pp.545–550(1997); and Yamachika et al.,Journal of Photopolymer Science and Technology, vol. 12 (No. 4), pp. 553–560 (1999).

One of important technical subjects on the resists for use in the lithography that uses a short-wavelength exposing source, represented by the ArF excimer laser, is to provide improved transparency to the exposing light of ray. This is because poor transparency lowers the resolution of the resist and worsens the pattern shape with trailing edges.

From such a viewpoint, unfortunately, though the above-mentioned triphenylsulfonium salt derivative is most widely used at present in the ArF excimer laser lithography as the photoacid generator consisting of a sulfonium salt compound, it has a disadvantage because its transparency is poor. That is, the triphenylsulfonium salt derivative has a benzene ring and thus strongly absorbs far UV rays not greater than 220 nm such as the ArF excimer laser characteristically. Accordingly, the triphenylsulfonium salt derivative is used as the photoacid generator to cause lower transparency of the resist. For example, see Naitoh Takuya, The 8th Research Group on Polymers for Microelectronics and Photonics, Proceedings, pp. 16–18 (1999).

Therefore, alkylsulfonium salt 2-oxocyclohexyl-methyl (2-norbornyl)sulfonium trifluoro methanesulfonate (NEALS), and cyclohexylmethyl(2-oxocyclo hexyl) sulfonium trifluoromethanesulfonate (ALS) are finally developed as new photoacid generators that are highly transparent against the ArF excimer laser. For example, see Proceeding of SPIE, vol. 2195, pp. 194–204 (1994); and Proceeding of SPIE, vol. 2438, pp. 433–444 (1995).

Though the above-mentioned newly developed photoacid generators consisting of sulfonium salt derivatives such as NEALS and ALS can improve transparency, they have disadvantages in sensitivity and thermal stability.

As for the sensitivity, in the ArF excimer laser lithography, a rate of sensitivity (exposure amount) of 20 mJ/cm$^2$ and below (ideally of 10 mJ/cm$^2$ and below) is required in general, though the above-mentioned NEALS requires an exposure amount of 50 mJ/cm$^2$ and above. Therefore, lowered sensitivity can not be avoided. On the other hand, as for the thermal stability, a thermal decomposition point in a resist film (resinous film) is about 120° C. and below, the upper temperature at the steps of heating during film formation of and after exposure to the resist is limited to about 120° C. In the resists in which the above-mentioned sulfonium salt derivatives are used as the photoacid generators, a process of heating at about 125° C. and above is required to release an acid even from unexposed parts by decomposition. This heating is impossible and their thermal stability lowers.

DISCLOSURE OF INVENTION

The present invention has been made in consideration of the above-mentioned situation and accordingly has an object to provide a photoacid generator capable of improving transmissivity and of preventing reduction of sensitivity and thermal stability, a photoresist composition containing the same and a method of pattering using the composition.

To solve the above-mentioned subject, the invention as described in claim 1 relates to a photoacid generator, comprising a sulfonium salt compound represented by general formula (1):

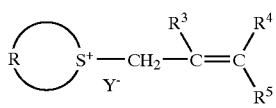

(1)

wherein R represents an alkylene group with or without an oxo group; R$^3$, R$^4$ and R$^5$ represent a hydrogen atom or a straight chain, branched, monocyclic, polycyclic or bridged cyclic alkyl group, and Y$^-$ represents a counter ion.

The invention as described in claim 2 relates to the photoacid generator according to claim 1, wherein R represents a alkylene group having 4 to 7 carbon atoms with or without an oxo group; R$^3$, R$^4$ and R$^5$ represent a hydrogen atom or a straight chain, branched, monocyclic, polycyclic or bridged cyclic alkyl group having 1 to 12 carbon atoms in the general formula (1).

The invention as described in claim 3 relates to a photoacid generator, comprising a sulfonium salt compound represented by general formula (2):

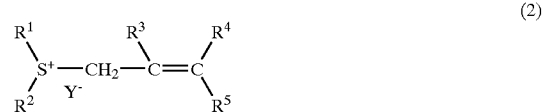

(2)

wherein R$^1$ and R$^2$ represent an alkyl group with or without an oxo group, or their cyclic alkylene group with or without an oxo group; R$^3$, R$^4$ and R$^5$ represent a hydrogen atom or a straight chain, branched, monocyclic, polycyclic or bridged cyclic alkyl group, and Y$^-$ represents a counter ion.

The invention as described in claim 4 relates to the photoacid generator according to claim 3, comprising a sulfonium salt compound, wherein R$^1$ and R$^2$ represent a alkyl group having 1 to 12 carbon atoms with or without an oxo group, or their cyclic alkylene group having 4 to 7 carbon atoms group with or without an oxo group; and R$^3$, R$^4$ and R$^5$ represent a hydrogen atom or a straight chain, branched, monocyclic, polycyclic or bridged cyclic alkyl group having 1 to 12 carbon atoms in the general formula (2).

The invention as described in claim 5 relates to the photoacid generator according to any one of claims 1–2, comprising a sulfonium salt compound, wherein the counter ion represented by Y$^-$ is Z—SO$_3^-$ (Z represents C$_n$F$_{2n+1}$ (n is 1–8), an alkyl group, an alkyl-substituted or non-substituted aromatic group), BF$_4^-$, AsF$_6^-$, SbF$_6^-$, ClO$_4^-$, Br$^-$, Cl$^-$ or I$^-$ in the general formula (1).

The invention as described in claim 6 relates to the photoacid generator according to any one of claims 3–4, comprising a sulfonium salt compound, wherein the counter ion represented by Y$^-$ is Z—SO$_3^-$ (Z represents C$_n$F$_{2n+1}$ (n is 1–8), an alkyl group, an alkyl-substituted or non-substituted aromatic group), BF$_4^-$, AsF$_6^-$, SbF$_6^-$, ClO$_4^-$, Br$^-$, Cl$^-$ or I$^-$ in the general formula (2).

The invention as described in claim 7 relates to a positive-type photoresist composition, containing the photoacid generator according to any one of claims 1–4.

The invention as described in claim 8 relates to a negative-type photoresist composition, containing the photoacid generator according to any one of claims 1–4.

The invention as described in claim 9 relates to a method of patterning, comprising the steps of: applying the photoresist composition according to claim 7 on a substrate to be processed; exposing said substrate to a ray of light with a wavelength of about 300 nm or below; and developing said substrate.

The invention as described in claim 10 relates to the method of patterning according to claim 9, wherein said ray of light for exposing is a KrF excimer laser.

The invention as described in claim 11 relates to the method of patterning according to claim 9, wherein said ray of light for exposing is an ArF excimer laser.

The invention as described in claim 12 relates to the method of patterning according to claim 9, wherein said ray of light for exposing is a F$_2$ excimer laser.

The invention as described in claim 13 relates to a method of patterning, comprising the steps of: applying the photoresist composition according to claim 8 on a substrate to be processed; exposing said substrate to a ray of light with a wavelength of about 300 nm or below; and developing said substrate.

The invention as described in claim 14 relates to the method of patterning according to claim 13, wherein said ray of light for exposing is a KrF excimer laser.

The invention as described in claim 15 relates to the method of patterning according to claim 13, wherein said ray of light for exposing is an ArF excimer laser.

The invention as described in claim 16 relates to the method of patterning according to claim 13, wherein said ray of light for exposing is a $F_2$ excimer laser.

BEST MODE FOR CARRYING OUT THE INVENTION

Figure 1:
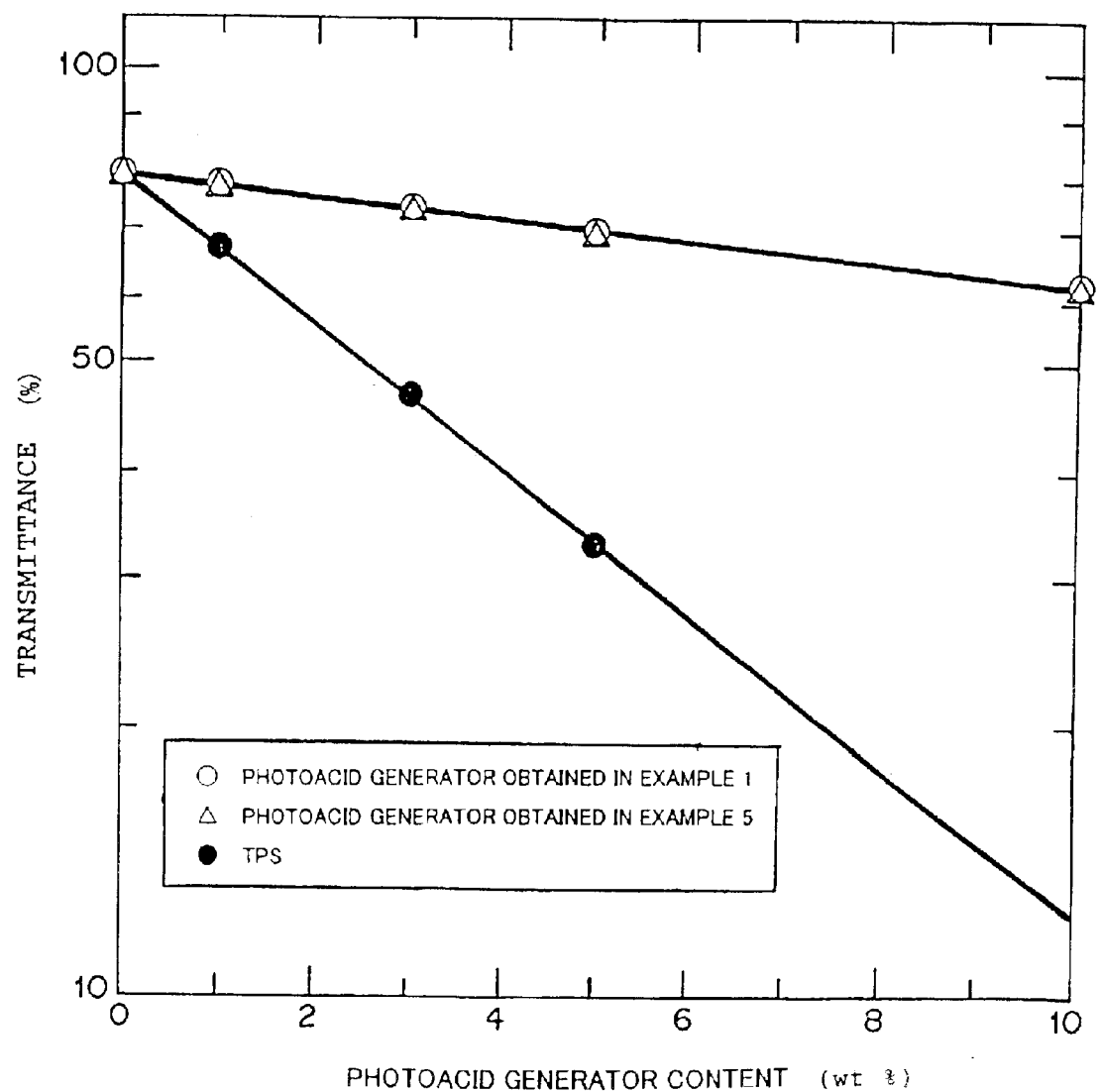
FIG. 1 is a diagram showing relations between transmittance and contents of photoacid generators in photoresist compositions obtained in examples of the present invention.

Presumptions:

Prior to description of embodiments according to the present invention, the presumptions for the present invention will be described generally.

The inventors have intensively studied to achieve the above-mentioned objects and finally completed the present invention. Namely, according to the present invention, a photoacid generator (sulfonium salt compound) is obtained, which has high transparency to the ArF excimer laser and thermal stability at about 150° C. or above even in resinous films. Specifically, the present invention is based on the finding that the above-mentioned subject can be solved by a photoacid generator consisting of a new alkylsulfonium salt compound with a structure disclosed below, a photoresist composition containing the photoacid generator as a component and a method of patterning in which patterning is carried out by light radiation using the photoresist composition.

In the above general formula (2), $R^1$ and $R^2$ may comprise an alkyl group or an alkyl group having an oxo group, or their cyclic alkylene group or their cyclic alkylene group having an oxo group.

Examples of the alkyl group include methyl group, ethyl group, propyl group, isopropyl group, butyl group, sec-butyl group, tert-butyl group, 2-methy-butyl group, 3-methy-butyl group, 3,3-dimethy-butyl group, pentyl group, 2-methyl-pentyl group, 3-methyl-pentyl group, 4-methyl-pentyl group, 4,4-dimethyl-pentyl group, 2-ethyl-pentyl group, 3-ethyl-pentyl group, hexyl group, 3-methyl-hexyl group, 4-methyl-hexyl group, 5-methyl-hexylgroup, 5,5-dimethyl-hexyl group, 2-ethyl-hexyl group, 3-ethyl-hexyl group, 4-ethyl-hexyl group, heptyl group, 2-methyl-heptyl group, 3-methyl-heptyl group, 4-methyl-heptyl group, 5-methyl-heptyl group, 6-methyl-heptyl group, 6,6-dimethyl-heptyl group, 2-ethyl-heptyl group, 3-ethyl-heptyl group, 4-ethyl-heptyl group, 5-ethyl-heptyl group, 2-ethyl-heptyl group, 3-ethyl-heptyl group, 4-propyl-heptyl group, octyl group, 2-methyl-octyl group, 3-methyl-octyl group, 4-methyl-octyl group, 5-methyl-octyl group, 6-methyl-octyl group, 7-methyl-octyl group, 7,7-dimethyl-octyl group, 2-ethyl-octyl group, 2-ethyl-octyl group, 3-ethyl-octyl group, 4-ethyl-octyl group, 5-ethyl-octyl group, cyclopentyl group, cyclohexyl group, cycloheptyl group, cyclopropylmethyl group, methylcyclohexyl group, cyclohexylmethyl group, norbornyl group, tricyclodecyl group (in particular, tricyclo [5.2.1.0$^{2,6}$]decyl group), adamantyl group, bornyl group, tetracyclododecyl group (in particular, tetracyclo [4.4.0$^{2,5}$.1$^{7,10}$]dodecyl group).

Examples of the alkyl group having an oxo group include 2-oxo-propyl group, 2-oxo-butyl group, 2-oxo-3-methy-butyl group, 2-oxo-3,3-dimethy-butyl group, 2-oxo-pentyl group, 2-oxo-3-methyl-pentyl group, 2-oxo-3,3-dimethyl-pentyl group, 2-oxo-4-methyl-pentyl group, 2-oxo-4,4-dimethyl-pentyl group, 2-oxo-3-ethyl-pentyl group, 2-oxo-3,3-diethyl-pentyl group, 2-oxo-4-methyl-4-ethyl-pentyl group, 2-oxo-hexyl group, 2-oxo-3-methyl-hexyl group, 2-oxo-3,3-dimethyl-hexyl group, 2-oxo-4,4-dimethyl-hexyl group, 2-oxo-5,5-dimethyl-hexyl group, 2-oxo-3-ethyl-hexyl group, 2-oxo-4-ethyl-hexyl group, 2-oxo-heptyl group, 2-oxo-3-methyl-heptyl group, 2-oxo-4-methyl-heptyl group, 2-oxo-5-methyl-heptyl group, 2-oxo-6-methyl-heptyl group, 2-oxo-6,6-dimethyl-heptyl group, 2-oxo-3-ethyl-heptyl group, 2-oxo-4-ethyl-heptyl group, 2-oxo-5-ethyl-heptyl group, 2-oxo-3-propyl-heptyl group, 2-oxo-4-propyl-heptyl group, 2-oxo-octyl group, 2-oxo-3-methyl-octyl group, 2-oxo-4-methyl-octyl group, 2-oxo-5-methyl-octyl group, 2-oxo-6-methyl-octyl group, 2-oxo-7-methyl-octyl group, 2-oxo-7,7-dimethyl-octyl group, 2-oxo-3-ethyl-octyl group, 2-oxo-4-ethyl-octyl group, 2-oxo-5-ethyl-octyl group, 2-oxo-cyclopentyl group, 2-oxo-cyclohexyl group, 2-oxo-cycloheptyl group, 2-oxo-cyclopropylmethyl group, 2-oxo-methylcyclohexyl group, 2-oxo-cyclohexylmethyl group, 2-oxo-norbornyl group, 2-oxo-tricyclodecyl group (in particular, 2-oxo-tricyclo[5.2.1.0$^{2,6}$]decyl group), 2-oxo-tetracyclododecyl group (in particular, 2-oxo-tetracyclo [4.4.0$^{2,5}$.1$^{7,10}$]dodecyl group), 2-oxo-bornyl group, 2-oxo-2-cyclohexyl-ethyl group and 2-oxo-2-cyclopentyl-ethyl group.

Examples of the cyclic alkylene group include propylene group, butylene group, pentylene group, hexylene group, heptylene group, oxopropylene group, oxobutylene group, oxopentylene group, oxohexylene group and oxoheptylene group.

$R^3$, $R^4$ and $R^5$ represent a hydrogen atom or a straight chain, branched, monocyclic, polycyclic or bridged cyclic alkyl group having 1 to 12 carbon atoms. Examples of the straight chain, branched, monocyclic, polycyclic or bridged cyclic alkyl group having 1 to 12 carbon atoms include methyl group, ethyl group, propyl group, isopropyl group, butyl group, sec-butyl group, tert-butyl group, 2-methy-butyl group, 3-methy-butyl group, 3,3-dimethy-butyl group, pentyl group, 2-methyl-pentyl group, 3-methyl-pentyl group, 4-methyl-pentyl group, 4,4-dimethyl-pentyl group, 2-ethyl-pentyl group, 3-ethyl-pentyl group, hexyl group, 3-methyl-hexyl group, 4-methyl-hexylgroup, 5-methyl-hexylgroup, 5,5-dimethyl-hexyl group, 2-ethyl-hexyl group, 3-ethyl-hexyl group, 4-ethyl-hexyl group, heptyl group, 2-methyl-heptyl group, 3-methyl-heptyl group, 4-methyl-heptyl group, 5-methyl-heptyl group, 6-methyl-heptyl group, 6,6-dimethyl-heptyl group, 2-ethyl-heptyl group, 3-ethyl-heptyl group, 4-ethyl-heptyl group, 5-ethyl-heptyl group, 2-ethyl-heptyl group, 3-ethyl-heptyl group, 4-propyl-heptyl group, octyl group, 2-methyl-octyl group, 3-methyl-octyl group, 4-methyl-octyl group, 5-methyl-octyl group, 6-methyl-octyl group, 7-methyl-octyl group, 7,7-dimethyl-octyl group, 2-ethyl-octyl group, 2-ethyl-octyl group, 3-ethyl-octyl group, 4-ethyl-octyl group, 5-ethyl-octyl group, cyclopentyl group, cyclohexyl group, cycloheptyl group, cyclopropylmethyl group, methylcyclohexyl group, cyclohexylmethyl group, norbornyl group, tricyclodecyl group (in particular, tricyclo [5.2.1.0$^{2,6}$]decyl group), adamantyl group, bornyl group and tetracyclododecyl group (in particular, tetracyclo [4.4.0$^{2,5}$.1$^{7,10}$]dodecyl group).

$Y^-$ represents a counter ion. Examples of the counter ion include $BF_4^-$ (tetrafluoroborato ion); $AsF_6^-$ (hexafluoroaresenate ion); $SbF_6^-$ (hexafluoroantimonate ion); $PF_6^-$ (hexafluorophosphate ion); ions of a sulfonic acid having a fluorocarbon group, such as $CF_3SO_3^-$ (trifluoromethanesulfonate ion), $C_2F_5SO_3^-$ (pentafluoroethanesulfonate ion), $C_3F_7SO_3^-$ (heptafluoropropanesulfonate ion), $C_4F_9SO_3^-$ (nonafluorobutanesulfonate ion), $C_5F_{11}SO_3^-$ (dodecafluoropentanesulfonate ion), $C_6F_{13}SO_3^-$ (tridecafluorohexanesulfonate ion), $C_7F_{15}SO_3^-$ (pentadecafluoroheptanesulfonate ion), $C_8F_{17}SO_3^-$ (heptadeca fluorooctanesulfonate ion), $C_9F_{19}SO_3^-$ (nonadecafluorononane sulfonate ion) and $C_{10}F_{21}SO_3^-$ (henycosafluorodecanesulfonate ion); ions of an alkylsulfonic acid, such as $CH_3SO_3^-$ (methanesulfonate ion), $C_2H_5SO_3^-$ (ethanesulfonate ion), $C_3H_7SO_3^-$ (propanesulfonate ion), $C_4H_8SO_3^-$ (butanesulfonate ion), $C_5H_{11}SO_3^-$ (pentanesulfonate ion), $C_6H_{13}SO_3^-$ (hexanesulfonate ion), $C_7H_{15}SO_3^-$ (heptanesulfonate ion), $C_8H_{17}SO_3^-$ (octanesulfonate ion), cyclohexansulfonate ion and camphorsulfonate ion; ions of a sulfonic acid having an aromatic group, such as benzenesulfonic acid ion, toluenesulfonic acid ion, naphthalenesulfonic acid ion, antracenesulfonic acid ion, fluorobenzenesulfonic acid ion, difluorobenzenesulfonic acid ion, trifluorobenzene sulfonic acid ion, chlorobenzenesulfonic acid ion, dichloro benzenesulfonic acid ion and trichlorobenzenesulfonic acid ion; $ClO_4^-$ (perchloric acid ion); $Br^-$ (bromine ion); $Cl^-$ (chlorine ion); and $I^-$ (iodine ion).

A method of synthesizing the sulfonium salt compound represented by general formula (2) according to the present invention is now exemplified. A sulfide compound represented by general formula (5):

is dissolved in acetonitrile, wherein $R^1$ and $R^2$ are the same as above, followed by adding a halogenated alkyl represented by general formula (6):

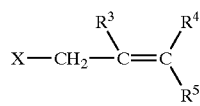

wherein $R^3$, $R^4$ and $R^5$ are the same as above; and X represents a halogen atom such as iodine, bromine and chlorine.

After agitation of the mixture for 0.5–24 hours, an organic metal represented by general formula (7):

is added, wherein Y is the same as above; and W represents a metal atom such as potassium, sodium and silver.

A halogenated metal salt precipitated is subjected to filtration and then its filtrate is distilled under reduced pressure to remove a solvent therefrom. A residue is rinsed with an appropriate solvent or recrystallized to obtain the sulfonium salt compound represented by general formula (2).

The sulfonium salt compound thus obtained and represented by general formula (2) is a new compound and is found to have extremely low optical absorption to ArF excimer laser compared to the known photoacid generator (triphenylsulfonium trifluoromethanesulfonate (hereinafter referred to as TPS) as described in the paper by Crivello et al.). The photoacid generator developed for KrF excimer laser lithography (TPS as described in the paper by Crivello et al.) has strong optical absorption to far UV ray such as ArF excimer laser. Therefore, if it is used as a photoacid generator for an ArF resist, it reduces the transparency of the resist remarkably. Compared to such TPS, the sulfonium salt derivatives as disclosed in the present invention have extremely low optical absorption to ArF excimer laser and are obviously suitable for a component of a resist for ArF excimer laser lithography with respect to transparency to a ray of exposing light. In addition to ArF excimer laser, they also have high transparency to KrF eximer laser and $F_2$ excimer laser. They can be used as photoacid generators for resists using these lasers as rays of exposing light.

The sulfonium salt compounds of the present invention are confirmed to have smaller amounts of rays of exposing light to generate an acid, that is, higher sensitivity compared to the conventional high transparent photoacid generators for ArF excimer laser lithography: alkylsulfonium salt 2-oxocyclohexyl-methyl(2-norbornyl)sulfonium trifluoromethanesulfonate(NEALS); and cyclohexylmethyl (2-oxocyclohexyl)sulfonium trifluoromethane sulfonate (ALS). It is also confirmed that they have higher thermal decomposition points and more excellent thermal stability compared to NEALS and ALS.

In the photoresist composition of the present invention, as described above, the chemically amplified resists of the positive type comprise at least three components: (1) a photoacid generator; (2) a base resin containing a group decomposable with acids; and (3) a solvent. On the other hand, the chemically amplified resists of the negative type are classified into two: one that essentially requires a crosslinking agent; and the other that requires no crosslinking agent. The former comprises at least four components: (1) a photoacid generator; (2) a base resin capable of reacting with a crosslinking agent; (3) a crosslinking agent; and (4) a solvent. The latter comprises at least three components: (1) a photoacid generator; (2) a base resin containing a crosslinking group; and (3) a solvent.

In the photoresist composition of the present invention, the sulfonium salt compound represented by general formula (2) can be used solely but may be used in combination of two or more such compounds. In the photoresist composition of the present invention, the alkylsulfonium salt compound represented by general formula (2) may be contained normally at 0.1–40 weight parts and preferably 1–25 weight parts per 100 weight parts of the total solid containing the compound itself. If the content is less than 0.1 weight part, the sensitivity of the present invention reduces remarkably and patterning is difficult. If it is more than 40 weight parts, formation of a uniform coating is difficult and residue or scum is easily generated after development disadvantageously.

A polymer that has high transparency in a region of far UV ray and contains an unstable group against a functional group and an acid may be set and used appropriately as a polymeric compound that is a constituent of the present invention. Namely, polymeric compounds represented by the general formulae (8)–(13) may be used, for example, as described later.

In the positive-type photoresist composition of the present invention, a resin that is highly transparent to an exposing wavelength, specifically a ray of exposing light, for example, ArF excimer laser and that can be solubilized in an alkaline developer by acidic action can be set and used appropriately. The content of the resin in 100 weight parts of the total components except for the solvent contained in the photoresist composition maybe normally at 60–99.8 weight parts, preferably 75–99 weight parts. Examples of resins preferably used for the positive-type photoresist composition of the present invention include the following resins. For example, a resin is disclosed in JP 2000-26446 A (JP Hei-10-188853 application) and represented by the following general formula (8):

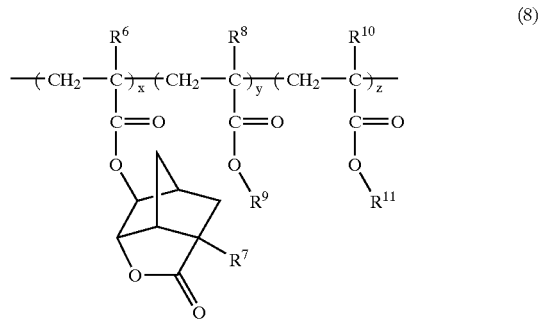

wherein $R^6$, $R^7$, $R^8$ and $R^{10}$ represent a hydrogen atom or a methyl group; $R^9$ represents a group decomposable with an acid, or a bridged cyclic hydrocarbon group having 7 to 13 carbon atoms having a group decomposable with an acid; $R^{11}$ represents a hydrogen atom, a hydrocarbon group having 1 to 12 carbon atoms, or a bridged cyclic hydrocarbon group having 7 to 13 carbon atoms having a carboxyl group; x, y and z represent arbitrary numbers satisfying $x+y+z=1$, $0<x<1$, $0<y<1$, $0\leq z<1$; and the polymer has a weight average molecular weight of 2000–200000.

Another resin is disclosed in Japanese Patent No. 2856116. It is represented by the following general formula (9):

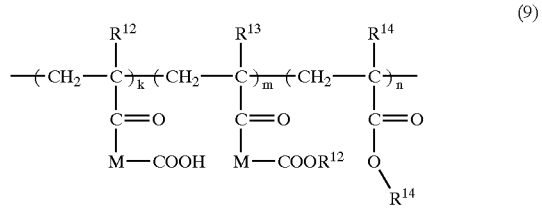

wherein $R^{12}$, $R^{13}$ and $R^{14}$ represent a hydrogen atom or a methyl group; M represents a group having a bridged cyclic hydrocarbon group having 7 to 13 carbon atoms; $R^{12}$ represents a group decomposable with an acid; $R^{14}$ represents a hydrogen atom or a hydrocarbon group having 1 to 12 carbon atoms; k, m and n represent arbitrary numbers satisfying $k+m+n=1$, $0<k<1$, $0<m<1$, $0\leq n<1$; and the polymer has a weight average molecular weight of 2000–200000.

A further resin is described in Journal of Photopolymer Science and Technology, vol. 10, No. 4, pp. 545–550 (1997). It is represented by the following general formula (10):

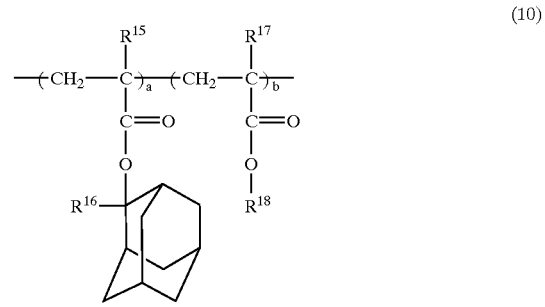

wherein $R^{15}$, $R^{16}$ and $R^{17}$ represent a hydrogen atom or a methyl group; $R^{12}$ represents a group having a lactone structure; a and b represent arbitrary numbers satisfying $a+b=1$, $0<a<1$, $0<b<1$; and the polymer has a weight average molecular weight of 2000–200000.

A further resin is described in Journal of Photopolymer Science and Technology, vol. 10, No. 3, pp. 511–520 (1997). It is represented by the following general formula (11):

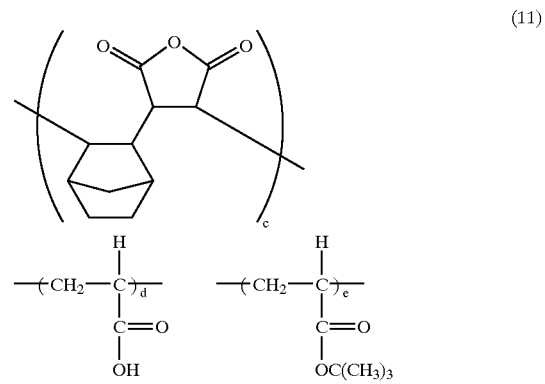

wherein c, d and e represent arbitrary numbers satisfying $c+d+e=1$, $0\leq c<1$, $0<d<1$, $0<e<1$; and the polymer has a weight average molecular weight of 2000–200000. As for resist resins of the positive type other than those herein specifically described, as long as they have the above high transparency and reactivity to an acid catalyst, they can be also used preferably. In a resist resin of the negative-type photoresist composition of the present invention, a resin that is highly transparent to a ray of exposing light, for example, ArF excimer laser and that can be insolubilized in an alkaline developer by an acidic action can be set and used appropriately. The content of the resin in 100 weight parts of the total components except for the solvent contained in the photoresist composition may be normally at 60–99.8 weight parts, preferably 75–99 weight parts. Examples of resins preferably used for the negative-type photoresist composition of the present invention include the following resins.

For example, a resin is described in Journal of Photopolymer Science and Technology, vol. 12, No. 3, pp. 487–492 (1999). It is represented by the following general formula (12):

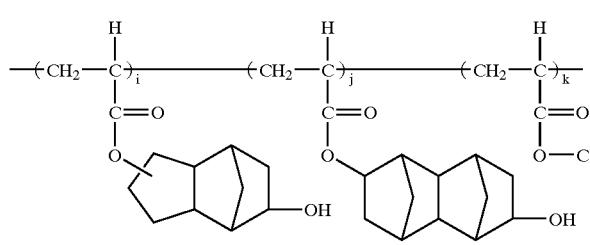

(12)

wherein i, j and k represent arbitrary numbers satisfying i+j+k=1, 0≦i<1, 0<j<1, 0≦k<1; and the polymer has a weight average molecular weight of 2000–200000. Another resin is represented by the following general formula (13):

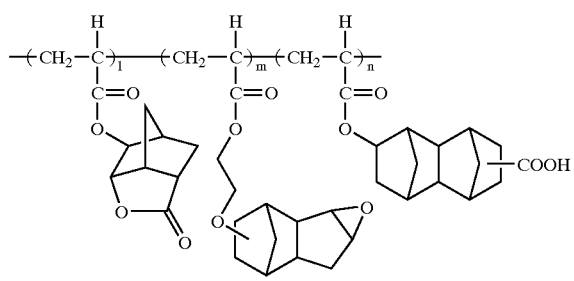

(13)

wherein l, m and n represent arbitrary numbers satisfying l+m+n=1, 0≦l<1, 0<m<1, 0<n<1; and the polymer has a weight average molecular weight of 2000–200000. As for resist resins of the negative type other than those herein specifically described, as long as they have the above high transparency and reactivity to an acid catalyst, they can be also used preferably.

In order to bridge and insolubilize the resin at an exposed part, a crosslinking agent may be added to the photoresist composition of the negative type. Preferred crosslinking agents include crosslinking agents of urea-melamine series and polyfunctional epoxy compounds, for example, hexamethoxy methylmelamine, 1,3,4,6-tetrakis(methoxymethyl) glycoluril, 1,3-bis(methoxymethyl)-4,5-bis (methoxymethyl)ethyleneurea and 1,3-bis(methoxymethyl) urea. Preferred crosslinking agents are not limited to those herein exemplified. In addition, they may be used solely or in combination of two or more thereof.

A polyhydric alcohol effective to improve a crosslinking density may be added as a crosslinking promoter. Examples of the crosslinking promoter include 2,3-dihydroxy-5-hydroxy methylnorbornane, 1,4-cyclohexanedimethanol and 3,4,8(9)-trihydroxytricyclodecane.

Solvents suitable for use in the photoresist composition of the present invention include any organic solvents so long as they can sufficiently dissolve the components consisting of a polymeric compound, a sulfonium salt and so forth, and the resulting solution can be used to form a uniform spin-coated film. They may be used solely or in combination of two or more thereof. Specifically, they include n-propyl alcohol, isopropyl alcohol, n-butyl alcohol, n-tert alcohol, methyl sellosolve acetate, ethylsellosolve acetate, propylene glycolmonoethyl ether acetate, methyl lactate, ethyl lactate, 2-methoxybutyl acetate, 2-ethoxyethyl acetate, methyl pyruvate, ethyl pyruvate, methyl 3-methoxypropionate, ethyl 3-methoxy propionate, N-methyl-2-pyrrolidinone, cyclohexane, cyclopentanone, cyclohexanol, methyl ethyl ketone, 1,4-dioxane, ethyleneglycolmonomethylether, ethyleneglycol monomethyl ether acetate, ethyleneglycolmonoethylether, ethyleneglycol monoisopropylether, diethyleneglycol monomethylether and diethyleneglycoldimethylether. They are not limited to the above-mentioned examples.

In addition to the above essential constituents in the photoresist composition, other components such as surfactants, colors, stabilizers, coating improving agents and dyes may be added, if required. A developer used in the present invention for forming a fine pattern may be selected according to the solubility of the polymeric compound used in the present invention from appropriate organic solvents; mixed solvents thereof; aqueous alkaline solutions with appropriate concentrations; and mixtures of the solutions with organic solvents. Other components such as a surfactant may be added to the developer, if required. The organic solvents to be used include acetone, methyl ethyl ketone, methyl alcohol, ethyl alcohol, isopropyl alcohol, tetrahydrofuran and dioxane. The alkaline solutions to be used include solutions or aqueous solutions that contain inorganic alkalis such as sodium hydroxide, potassium hydroxide, sodium silicate and ammonium; organic amines such as ethylamine, propylamine, diethylamine, dipropylamine, trimethylamine and triethylamine; and organic ammonium salts such as tetramethylammonium hydroxide, tetraethylammonium hydroxide, trimethylhydroxymethylammonium hydroxide, triethylhydroxymethylammonium hydroxide and trimethylhydroxyethylammonium hydroxide. They are not limited to the above-mentioned examples.

On the basis of the above-mentioned presumptions, embodiments of the present invention will now be described with reference to specific Examples.

EXAMPLE 1

2-methyl-2-propenyl-thiacyclopentanium trifluoro methanesulfonate was synthesized. This is represented by the following general formula (14):

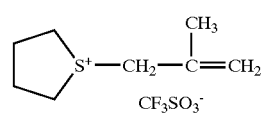

(14)

The following synthesis operations were performed under a yellow lamp.

One g of tetrahydrothiophene was dissolved in 20 ml of acetonitrile in a 100 ml, three-neck flask. Then, 0.94 g of 3-bromo-2-methyl-propene was dropped into the mixture under stirring. After agitation for 1 hour, a solution of 1.8 g of silver trifluoromethanesulfonate in 20 ml of acetonitrile was dropped into the mixture. After agitation for 3 hours, the resulting precipitated silver bromide was filtered. The filtrate was distilled under reduced pressure in an evaporator and the residue was washed three times with diethylether. Further, it was dissolved in 5 ml of acetone and the resulting solution was dropped into 300 ml of ether under stirring, resulting in a white crystal precipitated. After filtration, 1.4 g of 2-methyl-2-propenyl-thiacyclopentanium trifluoromethanesulfonate was obtained (with a yield of 68.5%). The melting point is 52.6° C.

Analyzed results by NMR and IR on the synthesized product are shown below:

$^1$H-NMR (CDCl$_3$, inner standard substance: tetramethyl silane): δ (ppm) 1.92 (s, 3H, —CH$_3$), 2.35–2.47 (m, 4H, —CH$_2$—), 3.39 (m, 1H, —CH$_3$—), 3.42 (m, 1H, —CH$_2$—), 3.95 (S, 4H, S$^+$—CH$_2$—), 5.23 (W, 2H, S$^+$—CH$_2$—C(=CH$_2$)—).

IR (KBr tablet, cm$^{-1}$) 2890 ($v_{C-H}$); 1642 ($v_{C=C}$); 1442, 1420 ($v_{C-H}$); 1258 ($v_{C-F}$); 1158, 1027($v_{SO3}$).

| Elementary analysis | C | H | S |
|---|---|---|---|
| Measured value (wt. %) | 36.71 | 5.30 | 22.02 |
| Theoretical value (wt. %) | 36.98 | 5.17 | 21.93 | wherein the theoretical value is a calculated value for C$_9$H$_{15}$F$_3$O$_3$S$_2$ (MW 292.33).

EXAMPLE 2

2-methyl-2-propenyl-thiacyclohexanium trifluoro methanesulfonate was synthesized. This is represented by the following general formula (15):

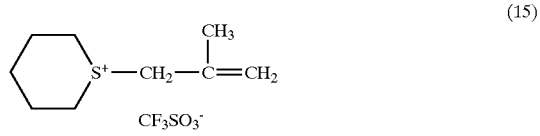

(15)

An experiment similar to Example 1 was performed using pentamethylenesulfide instead of tetrahydrothiophene, resulting in 1.68 g of 2-methyl-2-propenyl-thiacyclohexanium trifluoromethanesulfonate (with a yield of 78 %). Analyzed results by IR on the synthesized product are shown below:

IR (KBr tablet, cm$^{-1}$) 2961 ($v_{C-H}$); 1642 ($v_{C=C}$); 1442, 1422 ($v_{C-H}$); 1260 ($v_{C-F}$); 1152, 1029($v_{SO3}$).

| Measured value (wt. %) | 39.33 | 5.32 | 20.95 |
|---|---|---|---|
| Theoretical value (wt. %) | 39.21 | 5.59 | 20.93 | wherein the theoretical value is a calculated value for C$_{10}$H$_{17}$F$_3$O$_3$S$_2$ (MW 306.35).

EXAMPLE 3

2-methyl-2-propenyl-thiacyclohexanium nonafluoro butanesulfonate was synthesized. This is represented by the following general formula (16):

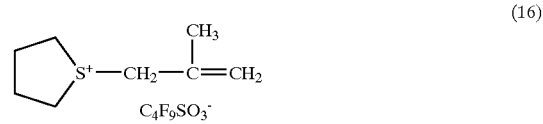

(16)

The following synthesis operations were performed under a yellow lamp.

In the same method as that of Example 1, using 2.37 g of potassium nonafluorobutanesulfonate instead of 1.8 g of potassium trifluoromethanesulfonate, an experiment was performed to synthesize 2-methyl-2-propenyl-thiacyclohexanium nonafluorobutanesulfonate, and 2.05 g of 2-methyl-2-propenyl-thiacyclohexanium nonafluorobutanesulfonate was obtained (with a yield of 66.2%). Analyzed results by IR on the synthesized product are shown below:

IR (KBr tablet, cm$^{-1}$) 2952 ($v_{C-H}$); 1644 ($v_{C=C}$); 1440, 1425 ($v_{C-H}$); 1259 ($v_{C-F}$); 1153, 1029($v_{SO3}$).

| Elementary analysis | C | H | S |
|---|---|---|---|
| Measured value (wt. %) | 32.5 | 3.66 | 13.63 |
| Theoretical value (wt. %) | 33.23 | 3.74 | 13.62 | wherein the theoretical value is a calculated value for C$_{12}$H$_{15}$F$_9$O$_3$S$_2$ (MW 442.35).

EXAMPLE 4

2-butenyl-thiacyclopentanium trifluoromethane sulfonate was synthesized. This is represented by the following general formula (17):

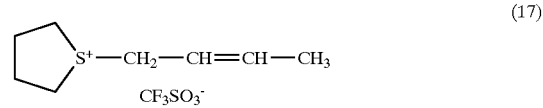

(17)

The following synthesis operations were performed under a yellow lamp.

2 g of tetrahydrothiophene was dissolved in 20 ml of acetonitrile in a 100 ml, three-neck flask. Then, 2.75 g of crotyl bromide was dropped into the mixture under stirring. After agitation for 1 hour, a solution of 5.1 g of silver trifluoromethanesulfonate in 20 ml of acetonitrile was dropped into the mixture. After agitation for 3 hours, the resulting precipitated silver bromide was filtered. The filtrate was distilled under reduced pressure in an evaporator and the residue was washed with diethylether. Further, it was dissolved in 5 ml of acetone and the resulting solution was dropped into 300 ml of ether under stirring, resulting in a white crystal precipitated. After filtration, 2.2 g of 2-butenyl-thiacyclopentanium trifluorobutane sulfonate was obtained (with a yield of 68.5 %). Analyzed results by IR on the synthesized product are shown below:

IR (KBr tablet, cm$^{-1}$) 2940 ($v_{C-H}$); 1650 ($v_{C=C}$); 1420 ($v_{C-H}$); 1260 ($v_{C-F}$); 1160, 1032($v_{SO3}$).

| Elementary analysis | C | H | S |
|---|---|---|---|
| Measured value (wt. %) | 37.00 | 5.20 | 21.77 |
| Theoretical value (wt. %) | 36.98 | 5.17 | 21.93 | wherein the theoretical value is a calculated value for $C_9H_{15}F_3O_3S_2$ (MW 292.33).

EXAMPLE 5

3-methyl-2-butenyl-thiacyclopentanium trifluoro methanesulfonate was synthesized. This is represented by the following general formula (18):

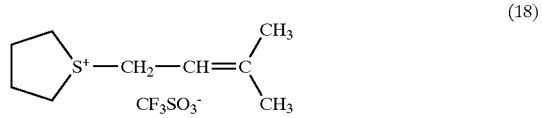

(18)

The following synthesis operations were performed under a yellow lamp.

2 g of tetrahydrothiophene was dissolved in 20 ml of acetonitrile in a 100 ml, three-neck flask. Then, 2.98 g of bromomethylbutene was dropped into the mixture under stirring. After agitation for 1 hour, a solution of 5.1 g of silver trifluoromethanesulfonate in 20 ml of acetonitrile was dropped into the mixture. After agitation for 3 hours, the resulting precipitated silver bromide was filtered. The filtrate was distilled under reduced pressure in an evaporator and the residue was washed with diethylether. Further, it was dissolved in 5 ml of acetone and the resulting solution was dropped into 300 ml of ether under stirring, resulting in a white crystal precipitated. After filtration, 2.2 g of 3-methyl-2-butenyl-thiacyclopentanium trifluoro methanesulfonate was obtained (with a yield of 68.5 ). Analyzed results by IR on the synthesized product are shown below:

IR (KBr tablet, cm$^{-1}$) 2982 ($v_{C-H}$); 1650 ($v_{C-C}$); 1450, 1429 ($v_{C-H}$); 1264 ($v_{C-F}$); 1160, 1030($v_{SO3}$).

| Elementary analysis | C | H | S |
|---|---|---|---|
| Measured value (wt. %) | 39.25 | 5.59 | 20.81 |
| Theoretical value (wt. %) | 39.21 | 5.59 | 20.93 | wherein the theoretical value is a calculated value for $C_{10}H_{17}F_3O_3S_2$ (MW 306.35).

EXAMPLE 6

2-methyl-1-propenyl-diethylsulfonium trifluoromethane sulfonate was synthesized. This is represented by the following general formula (19):

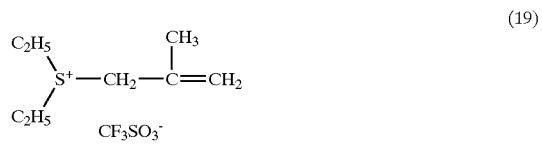

(19)

The following synthesis operations were performed under a yellow lamp.

1.5 g of diethylsulfide was dissolved in 20 ml of acetonitrile in a 100 ml, three-neck flask. Then, 2.5 g of bromomethylbutene was dropped into the mixture under stirring. After agitation for 1 hour, a solution of 4.2 g of silver trifluoromethanesulfonate in 20 ml of acetonitrile was dropped into the mixture. After agitation for 3 hours, the resulting precipitated silver bromide was filtered. The filtrate was distilled under reduced pressure in an evaporator and the residue was washed with diethylether. Further, it was dissolved in 5 ml of acetone and the resulting solution was dropped into 300 ml of ether under stirring, resulting in a white crystal precipitated. After filtration and then re-crystallization in ethyl acetate, 3.2 g of 2-methyl-1-propenyl-diethylsulfonium trifluoromethanesulfonate was obtained (with a yield of 65.9 %). Analyzed results by IR on the synthesized product are shown below:

IR (KBr tablet, cm$^{-1}$) 2982 ($v_{C-H}$); 1650 ($v_{C=C}$); 1447, 1429 ($v_{C-H}$); 1264 ($v_{C-F}$); 1160, 1030($v_{SO3}$).

| Elementary analysis | C | H | S |
|---|---|---|---|
| Measured value (wt. %) | 36.72 | 5.82 | 21.78 |
| Theoretical value (wt. %) | 36.94 | 5.74 | 22.03 | wherein the theoretical value is a calculated value for $C_9H_{17}F_3O_3S_2$ (MW 294.3).

Experimental Example 1

Evaluation on Thermal Stability in Resinous Films

Films (0.4 μm thick) of poly(methyl methacrylate 40-tert-butylmethacrylate 40-methacrylic acid 20) each containing 1 wt. % of the respective photoacid generators obtained in Examples 1–5 were heated on a hot plate at a predetermined temperature for 60 seconds. Immediately after heating, they were cooled down to room temperature and then immersed for 60 seconds into a developer (2.38 wt. % tetramethylammoniumhydroxide (an aqueous solution of TMAH)). As a result, decomposition points corresponding to the photoacid generators were obtained as shown in Table 1.

When a sulfonium salt compound is decomposed thermally, an acid decomposes a protection group (tert-butyl group) of the resin to make the resin soluble in the developer. Accordingly, when the resinous film is heated and dissolved in the developer, the heating temperature is defined as the thermal decomposition point of the sulfonium salt compound in the resinous film. As obvious from Table 1, the thermal decomposition point of the sulfonium salt compound in the resinous film obtained in Example 1 of the present invention is 135° C., which is more excellent in thermal stability than 2-oxocyclohexylmethyl (2-norbornyl) sulfonium triflate (with a thermal decomposition point of 125° C.).

TABLE 1

| Photoacid generator | Decomposition point |
|---|---|
| Photoacid generator obtained in Example 1 | 153° C. |
| Photoacid generator obtained in Example 2 | 151° C. |
| Photoacid generator obtained in Example 3 | 155° C. |
| Photoacid generator obtained in Example 4 | 152° C. |
| Photoacid generator obtained in Example 5 | 153° C. |
| 2-oxocyclohexylmethyl(2-norbornyl)sulfonium triflate | 125° C. |

EXPERIMENTAL EXAMPLE 2
Measurement of Transmittance of Resinous Film Containing Alkylsulfonium Salt 1.5 g of polymethyl methacrylate (PMMA) and the sulfonium salts obtained in Example 1 and 5 were dissolved in ethyl lactate, then the resulting solution was filtered through a membrane filter, further the filtrate was rotationally coated on a 3-inch quartz substrate, and finally the coated sample was heated on a hot plate at 120° C. for 60 seconds. Through these operations, a resinous film with a thickness of about 0.5 μm was obtained. As for the film obtained, the transmittance at 193.4 nm was measured using a visible UV spectrophotometer (UV-365). Also as for a comparative example of a resinous film that contains triphenylsulfonium trifluoromethanesulfonate (TPS) with benzene ring(s), the transmittance was measured. It can be found from measured results shown in FIG. 1 that the resinous films containing the sulfonium salts obtained in Examples 1–6 exhibit less reduction in transmittance than the resinous film that contains triphenylsulfonium trifluoro methanesulfonate.

EXPERIMENTAL EXAMPLE 3
Evaluation on Patterning by Positive Resists Using Sulfonium Salts A resist consisting of the following composition was prepared:
(a) 2 g of a resin having a structure represented by the following formula (20);

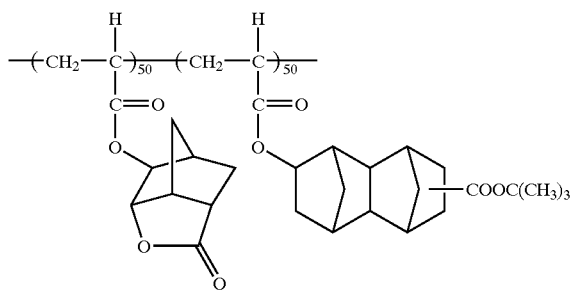

(20)

(b) 0.02 g of a photoacid generator (the photoacid generators obtained in Examples 1–6); and
(c) 11.5 g of propyleneglycolmonomethylether acetate.

The above mixture was filtered using a 0.2 μm Teflon (trademark) filter to prepare a resist. The resist was spin-coated over a 4-inch silicon substrate and baked at 130° C. for 1 minute on a hot plate to form a thin film with a thickness of 0.4 μm. The wafer coated with the resist was placed stationarily in a fully nitrogen-purged contact-type exposure experimental machine. A mask that had chromium patterns depicted on a quartz plate was tightly contacted on the resist film, which was exposed through the mask with ArF excimer laser. Immediately after exposure, it was baked at 110° C. for 60 seconds on a hot plate, developed by an immersion technology in an aqueous solution of 2.38% TMAH at a solution temperature of 23° C., subsequently rinsed with pure water for 60 seconds. Obtained was a pattern of the positive type, from which only exposed parts of the resist film were dissolved in the developer and removed.

As Comparative examples, resists that used 2-oxocyclohexylmethyl(2-norbornyl) sulfonium triflato (NEALS) and triphenylsulfonium trifluoromethanesulfonate (TPS) for photoacid generators were evaluated in a similar way. Table 2 shows results on sensitivity and resolution. As obvious from Table 2, the photoresist compositions of the positive type using the sulfonium salts of the present invention are excellent in resolution.

TABLE 2

|  | Resolution (μmL/S) | Sensitivity (mJ/cm³) |
|---|---|---|
| Resist containing Photoacid generator in Example 1 | 0.17 | 7.5 |
| Resist containing Photoacid generator in Example 2 | 0.17 | 9 |
| Resist containing Photoacid generator in Example 3 | 0.16 | 8.5 |
| Resist containing Photoacid generator in Example 4 | 0.17 | 7.7 |
| Resist containing Photoacid generator in Example 5 | 0.17 | 7.6 |
| Resist containing Photoacid generator in Example 6 | 0.19 | 12.3 |
| Comparative example 1 (Resist containing NEALS) | 0.19 | 50.8 |
| Comparative example 2 (Resist containing TPS) | 0.19 | 6.5 |

EXPERIMENTAL EXAMPLE 4
Evaluation on Patterning by Negative Resists Using Sulfonium Salts A resist consisting of the following composition was prepared:
(a) 2 g of a resin having a structure represented by the following formula (21);

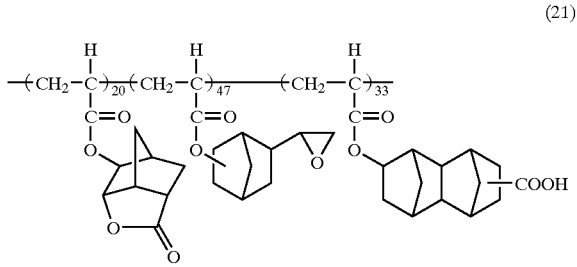

(21)

(b) 0.04 g of a photoacid generator (the sulfonium salts obtained in Examples 1–3);
(c) 0.3 g of 2,3-dihydroxy-5-hydroxymethylnorbornane; and
(d) 11.5 g of ethyl lactate.

The above mixture was filtered using a 0.2 μm Teflon filter to prepare a resist. The resist was spin-coated over a 4-inch silicon substrate and baked at 80° C. for 1 minute on a hot plate to form a thin film with a thickness of 0.4 μm. The wafer coated with the resist was placed stationarily in a fully nitrogen-purged contact-type exposure experimental machine. A mask that had chromium patterns depicted on a quartz plate was tightly contacted on the resist film, which was exposed through the mask with ArF excimer laser. Immediately after exposure, it was baked at 130° C. for 60 seconds on a hot plate, developed by an immersion-technology in an aqueous solution of 2.38% TMAH at a solution temperature of 23° C., subsequently rinsed with pure water for 60 seconds. Obtained was a pattern of the negative type, from which only unexposed parts of the resist film were dissolved in the developer and removed.

As Comparative examples, resists of the negative type that used 2-oxocyclohexyl methyl(2-norbornyl)sulfonium triflato (NEALS) and triphenyl sulfonium trifluoromethane-sulfonate (TPS) were evaluated in a similar way. Table 3 shows results on sensitivity and resolution. As obvious from Table 3, the photoresist compositions of the negative type using the sulfonium salts of the present invention are excellent in resolution.

TABLE 3

| | Resolution (μmL/S) | Sensitivity (mJ/cm³) |
|---|---|---|
| Resist containing Sulfonium salt in Example 1 | 0.18 | 7.8 |
| Resist containing Sulfonium salt in Example 2 | 0.18 | 8.8 |
| Resist containing Sulfonium salt in Example 3 | 0.17 | 8.9 |
| Comparative example 1 (Resist containing NEALS) | 0.20 | 49 |
| Comparative example 2 (Resist containing TPS) | 0.19 | 6.8 |

The embodiments consistent with the present invention with reference to the drawing have been described as mentioned above, but specific configurations are not limited to the above-mentioned embodiments. Modification and variations consistent with the invention can be contained within the scope of the appended claims. For example, the present invention is exemplified particularly in application to the production of semiconductor devices in the description, though it is not limited to these and is rather applicable similarly to fields that require micro processing of various conductors and insulators. In addition, the synthesis conditions and so forth indicated in Examples are just exemplification and can be altered in accordance with the purpose, use and the like.

Industrial Applicability

As obvious from the forgoing, according to the photoacid generator, the photoresist composition containing the photoacid generator, and the method of patterning using the photoresist composition, such sulfonium salt compounds can be obtained that are excellent in transparency to far UV rays, typically represented by ArF excimer laser. In addition, the resist that uses the sulfonium salt compound as the photoacid generator can be excellent in resolution.

Therefore, the present invention can provide a photoacid generator capable of improving transmittance and of preventing reduction of sensitivity and thermal stability, a photoresist composition containing the same and a method of pattering using the composition.

What is claimed is:

1. A photoacid generator, comprising a sulfonium salt compound represented by general formula (1):

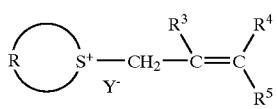

(1)

wherein R represents an alkylene group with or without an oxo group; $R^3$, $R^4$ and $R^5$ represent a hydrogen atom or a straight chain, branched, monocyclic, polycyclic or bridged cyclic alkyl group, and Y— represents a counter ion.

2. The photoacid generator according to claim 1, wherein R represents a alkylene group having 4 to 7 carbon atoms with or without an oxo group; $R^3$, $R^4$ and $R^5$ represent a hydrogen atom or a straight chain, branched, monocyclic, polycyclic or bridged cyclic alkyl group having 1 to 12 carbon atoms in the general formula (1).

3. The photoacid generator according to claim 2, wherein said counter ion represented by Y— comprises one of Z—SO$_3$— (Z represents $C_nF_{2n+1}$ (n is an integer between 1 and 8), an alkyl group, an alkyl-substituted or non-substituted aromatic group), BF$_4$—, AsF$_6$—, SbF$_6$—, ClO$_4$—, Br—, Cl— and I— in the general formula (1).

4. A positive-type photoresist composition, comprising the photoacid generator according to claim 2.

5. A negative-type photoresist composition, comprising the photoacid generator according to claim 2.

6. A method of patterning, comprising:
applying the photoresist composition according to claim 4 on a substrate in be processed;
exposing said substrate to a ray of light with a wavelength of about 300 nm or less; and
developing said substrate.

7. The method patterning according to claim 6, wherein said ray of light for exposing comprises a KrF excimer laser light.

8. The method of patterning according to claim 6, wherein said ray of light for exposing comprises one of an ArF excimer laser light and a F$_2$ excimer laser light.

9. A method of patterning, comprising:
applying the photoresist composition according to claim 5 on a substrate to be processed; exposing said substrate to a ray of light with a wavelength of about 300 nm or less; and developing said substrate.

10. The method of patterning according to claim 9, wherein said ray of light for exposing comprises a KrF excimer laser light.

11. The method of patterning according to claim 9, wherein said ray of light for exposing comprises one of an ArF excimer laser light and a F$_2$ excimer laser light.

12. A positive-type photoresist composition, comprising a photoacid generator, comprising a sulfonium salt compound represented by general formula (2):

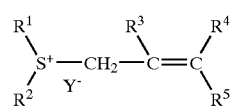

(2)

wherein $R^1$ and $R^2$ represent an alkyl group with or without an oxo group, or $R^1$ and $R^2$ are linked to each other to form a cyclic alkylene group with or without an oxo group,
wherein $R^3$, $R^4$ and $R^5$ represent one of a hydrogen atom and a straight chain, branched, monocyclic, polycyclic or bridged cyclic alkyl group, and Y$^-$ represents a counter ion.

13. A negative-type photoresist composition, comprising a photoacid generator, comprising a sulfonium salt compound represented by general formula (2):

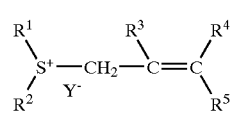

(2)

wherein $R^1$ and $R^2$ represent an alkyl group with or without an oxo group, or $R^1$ and $R^2$ are linked to each other to form a cyclic alkylene group with or without an oxo group, wherein $R^3$, $R^4$ and $R^5$ represent one of a hydrogen atom and a straight chain, branched, monocyclic, polycyclic or bridged cyclic alkyl group, and $Y^-$ represents a counter ion.

14. A method of patterning, comprising:

applying the photoresist composition according claim 12 a substrate to be processed;

exposing said substrate to a ray of light with a wavelength of about 300 nm or less; and developing said substrate.

15. A method of patterning, comprising:

applying the photoresist composition according to claim 13 on a substrate to be processed;

exposing said substrate to a ray of light with a wavelength of about 300 nm or less; and developing said substrate.

16. The method of patterning according to claim 14, wherein said ray of light for exposing comprises a KrF excimer laser light.

17. The method of patterning according to claim 15, wherein said ray of light for exposing comprises a KrF excimer laser light.

18. The method of patterning according to claim 14, wherein said ray of light for exposing comprises one of an ArF excimer laser light and a $F_2$ excimer laser light.

19. The method of patterning according to claim 15, wherein said ray of light for exposing comprises one of an ArF excimer laser light and a $F_2$ excimer laser light.

* * * * *

UNITED STATES PATENT AND TRADEMARK OFFICE
CERTIFICATE OF CORRECTION

PATENT NO. : 6,849,384 B2  Page 1 of 1
DATED : February 1, 2005
INVENTOR(S) : Shigeyuki Iwasa et al.

It is certified that error appears in the above-identified patent and that said Letters Patent is hereby corrected as shown below:

<u>Title page, Item [54] and Column 1, lines 1-4,</u>
Title, should read as follows:
-- PHOTOACID GENERATORS, PHOTORESIST COMPOSITIONS CONTAINING THE SAME AND PATTERNING METHOD WITH THE USE OF THE COMPOSITIONS --.

Signed and Sealed this

Sixteenth Day of August, 2005

JON W. DUDAS
*Director of the United States Patent and Trademark Office*